(12) United States Patent
Owens et al.

(10) Patent No.: US 10,377,690 B1
(45) Date of Patent: Aug. 13, 2019

(54) METHOD FOR CATALYTIC PRODUCTION OF REFINED ENAL PRODUCTS FROM AN ALDEHYDE FEED STREAM USING A SINGLE ENCLOSED UNIT

(71) Applicant: Eastman Chemical Company, Kingsport, TN (US)

(72) Inventors: Scott Allen Owens, Kingsport, TN (US); Robert Lin, Kingsport, TN (US); Jody Lee Rodgers, Gilmer, TX (US)

(73) Assignee: Eastman Chemical Company, Kingsport, TN (US)

( * ) Notice: Subject to any disclaimer, the term of this patent is extended or adjusted under 35 U.S.C. 154(b) by 0 days.

(21) Appl. No.: 16/109,115

(22) Filed: Aug. 22, 2018

(51) Int. Cl.
| | | |
|---|---|---|
| *C07C 45/73* | (2006.01) | |
| *B01D 3/00* | (2006.01) | |
| *C07C 45/74* | (2006.01) | |
| *B01D 3/14* | (2006.01) | |
| *C07C 47/20* | (2006.01) | |

(52) U.S. Cl.
CPC .............. *C07C 45/74* (2013.01); *B01D 3/143* (2013.01); *C07C 47/20* (2013.01); *C07B 2200/09* (2013.01)

(58) Field of Classification Search
CPC .......... C07C 45/73; C07C 45/74; B01D 3/141
See application file for complete search history.

(56) References Cited

U.S. PATENT DOCUMENTS

| | | |
|---|---|---|
| 3,248,428 A | 4/1966 | Porter, Jr. et al. |
| 4,684,750 A | 8/1987 | Kessen et al. |
| 5,227,544 A | 7/1993 | Thurman et al. |
| 6,930,206 B1 | 8/2005 | Groten et al. |
| 6,960,694 B2 | 11/2005 | Barnicki et al. |
| 8,764,946 B2 | 7/2014 | Lee et al. |
| 8,791,304 B2 | 7/2014 | Ko et al. |
| 8,852,405 B2 | 10/2014 | Lee et al. |
| 8,952,189 B2 | 2/2015 | Dux et al. |
| 9,035,110 B2 | 5/2015 | Krokoszinski et al. |
| 9,181,156 B2 | 11/2015 | Ko et al. |
| 2012/0245385 A1 | 9/2012 | Sander et al. |
| 2016/0176797 A1 | 6/2016 | Brueggemann et al. |
| 2017/0240487 A1 | 8/2017 | Tinger et al. |

FOREIGN PATENT DOCUMENTS

| | | |
|---|---|---|
| CN | 101328119 A | 12/2008 |
| CN | 103864587 A | 6/2014 |
| EP | 2796440 A1 | 10/2014 |
| KR | 20130018427 A | 2/2013 |

OTHER PUBLICATIONS

Sander, Stefan; "Two process steps in one column", Chemical Plants & Processes; Oct. 2007.
Khushalani, Kishore, et al.; "Separation of Mixture by Divided Wall Column using ASPEN PLUS", International Journal of Emerging Technology and Advanced Engineering; vol. 4, Issue 8, Aug. 2014.
Eden, Dr. Mario Richard; "CHEN 4470—Process Design Practice"; Department of Chemical Engineering Auburn University, Lecture No. 12—Advanced Distillation Column Modeling and Reactive Distillation, Feb. 26, 2013http://wp.auburn.edu/eden/wp-content/uploads/2012/03/4470-Lecture-12-2013.ppt.
"Simulate a Reactive Distillation Column with Aspen Plus V8.0", https://lms.nchu.edu.tw/sysdata/doc/6/6a4974d4249fcc8a/pdf.pdf Revised Oct. 31, 2012.

*Primary Examiner* — Sikarl A Witherspoon
(74) *Attorney, Agent, or Firm* — Kenrick L. Vidale

(57) ABSTRACT

Disclosed is a method for forming enals from corresponding alehydes in a single enclosed unit such as a divided wall reaction distillation unit. The method of the present invention includes (a) feeding an aldehyde feed stream comprising at least one aldehyde reactant into a reaction zone contained within said single enclosed unit; (b) reacting said at least one aldehyde reactant in said reaction zone in the presence of a catalyst to form an enal-containing reaction zone effluent comprising an enal; (c) purifying said enal-containing reaction zone effluent in a first separation zone within said single enclosed unit to form an enal-rich product mixture and a residual unreacted aldehyde mixture; and (d) collecting from said single enclosed unit at least a portion of said enal-rich product mixture. The method of the present invention results in high enal yields at a markedly reduced capital cost and energy consumption as compared to prior art processes.

19 Claims, 5 Drawing Sheets

Fig 1 – Prior Art

METHOD FOR CATALYTIC PRODUCTION OF REFINED ENAL PRODUCTS FROM AN ALDEHYDE FEED STREAM USING A SINGLE ENCLOSED UNIT

FIELD OF THE INVENTION

The present invention generally relates to method for catalytic synthesis and purification of enals in a single enclosed processing unit or piece of equipment such as a divided wall reactive distillation unit.

BACKGROUND OF THE INVENTION

It is known in the art to manufacture enals via catalytic reaction of aldehydes, aldehyde mixtures or aldehyde/alcohol mixtures. In a typical process, reactant aldehydes/alcohols are fed to a reactor. If a homogenous catalyst is used, it is co-fed to the reactor. If a heterogenous catalyst is used it is charged to the reaction vessel prior to start-up. The reaction products are then fed to a separation train wherein water, light, and heavy by-products are removed from desired products of the reaction. This train typically consists of at least two distillation columns for the removal of heavy and light boiling component. A decanter may be inserted between the reactor and distillation device to assist in removing any free water present in the reaction product. When using a homogenous catalyst, the aqueous phase contains catalyst and may be recycled to the reactor feed. A purge stream can be taken off this recycle. This general process and equipment configuration is diagrammed generically in FIG. 1 herein. The reaction is a condensation reaction and is often referred to the art as "aldol condensation". Aldol condensation is used to describe a class of condensation reactions wherein a carbonyl reacts with another carbonyl or an alkenol to form a hydroxylaldehyde or hydroxyketone which is then (with sufficiently high reaction system temperature) subjected to dehydration to give an enal or enone product, respectively.

Specific examples and variations of the above generic approach are described for example in U.S. Pat. Nos. 4,684,750; 5,227,544; 8,791,304 B2 and 9,181,156 B2. More specifically, the '750, '544 and '156 patents describe the aldol condensation of n-butanal with itself in the presence of an alkali catalyst to form butyraldol and the subsequent dehydrogenation to form 2-ethylhexanol and the '304 patent describes the use of a continuous-stirred tank reactor to conduct the aldol condensation.

The prior art processes for forming enals from aldehydes using aldol condensation have a number of drawbacks. First, they typically require multiple complex engineered vessels and pieces of processing equipment assembled in series, which translates to a large initial capital expenditure for plant construction and significant ongoing equipment maintenance, repair and/or replacement costs. Further, each piece of equipment is typically designed and/or operated to facilitate long residence times and other conditions that can be required to maximize reactant conversion. For example, reactors are typically stirred tank reactors with very large volumes or pipe reactors with very long pipe runs and/or multiple catalyst injections. Similarly, distillation columns are often operated at high recycle levels such that the majority of the reactor effluent is returned to the reactor feed. The push to maximize conversion often results in extremely high energy use (and energy cost) as well as extended periods, sometimes hours, wherein reactants, products, and catalyst are all simultaneously exposed to each other. This extended exposure can be highly undesirable and result in unintended side-reactions, production of contaminating by-products and reduction of yield and production efficiency.

A continuing need therefore exists for a method for forming aldol condensation products that has lower capital construction, maintenance, energy use and operating costs while achieving high product conversion and yields with minimized contaminant and/or by-product formation.

SUMMARY OF THE INVENTION

In a first aspect, the present invention relates to a method for producing an enal-rich product mixture from an aldehyde feed stream in a single enclosed unit or vessel, said method comprising (a) feeding an aldehyde feed stream comprising at least one aldehyde reactant into a reaction zone contained within said single enclosed unit; (b) reacting said aldehyde reactant in said reaction zone in the presence of a catalyst to form a light reaction zone effluent comprising an enal and unreacted aldehyde reactant; (c) purifying said light reaction zone effluent in a first separation zone within said single enclosed unit to form an enal-rich product mixture and a residual unreacted aldehyde mixture; and (d) collecting from said single enclosed unit at least a portion of said enal-rich product mixture; wherein said collected portion includes at least 60% by weight enal based on the total weight of the organic fraction of the enal-rich product mixture.

In a second aspect, the present invention relates to an enal/aldehyde catalytic conversion device.

Further aspects of the invention are as disclosed and claimed herein.

DETAILED DESCRIPTION

Figure 1:
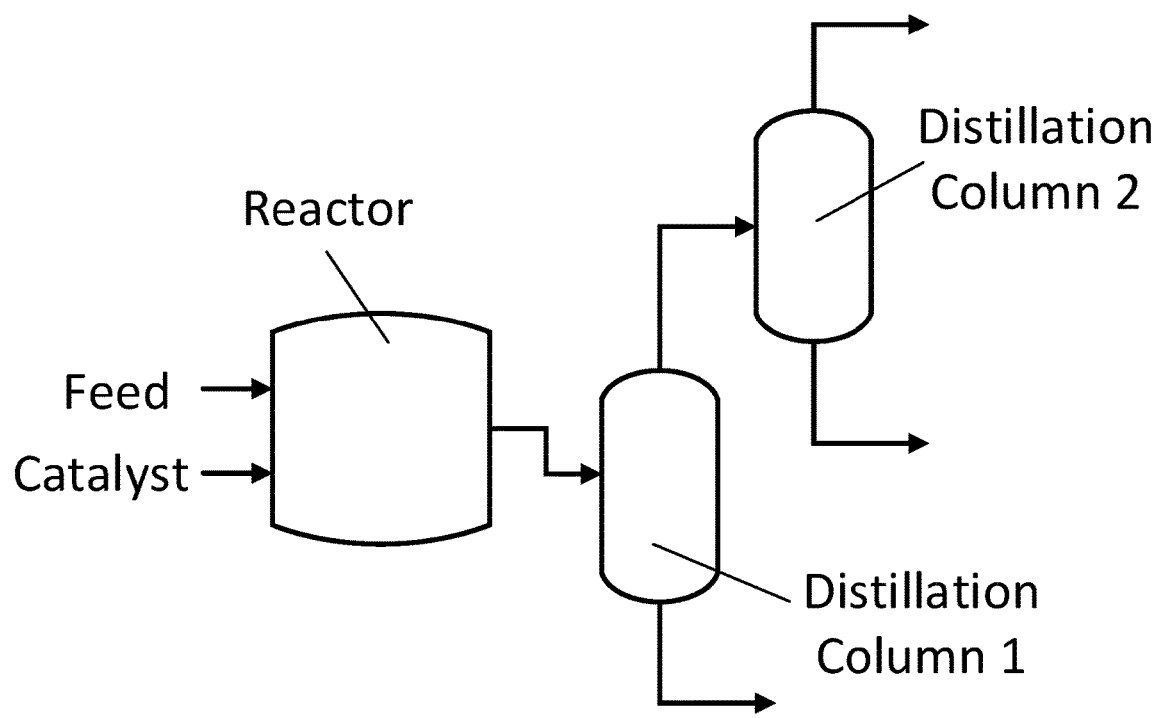
FIG. 1 is a generic schematic flow representation of prior art methodology for aldol condensation reactions.

The first aspect of the present invention is method for forming aldol condensation products from aldehydes in a single enclosed unit or vessel, for example a divided wall reaction distillation unit. The method of the present invention includes (a) feeding an aldehyde feed stream comprising at least one aldehyde reactant into a reaction zone contained within said single enclosed unit; (b) reacting said aldehyde reactant in said reaction zone in the presence of a catalyst to form a light reaction zone effluent that includes enal product and unreacted aldehyde reactant and optionally any light feed impurities and water; (c) purifying said light reaction zone effluent in a first separation zone within said single enclosed unit to form an enal-rich product mixture and a residual unreacted aldehyde mixture; and (d) collecting from said single enclosed unit at least a portion of the enal-rich product mixture; wherein said collected portion includes at least 60% by weight, more preferably at least 80% by weight enal based on the total weight of the organic fraction of the enal-rich product mixture. The term "effluent", as used herein, is intended to generally refer to a composition or mixture (i) present in the reaction zone as well as (ii) exiting the reaction zone.

The aldehyde feed stream of the feeding step (a) of the method of the present invention preferably includes at least one aldehyde reactant. Suitable aldehyde reactants will be apparent to one ordinary skill and include, but are not limited to, acetaldehyde, propionaldehyde, butyraldehyde, valeraldehyde, capronaldehyde, their isomers, and mixtures thereof. Particularly suitable aldehyde reactants include, but are not limited to, propionaldehyde (forming C6 enal in the method of the present invention) or butyraldehyde (forming C8 enal as in the method of the present invention). The reactant in some embodiments may include two or more aldehydes, or a mixture of at least one aldehyde and at least one alcohol including, but not limited to, propanol or butanol. The aldehyde feed stream of the feeding step (a) of the method of the present invention may also include other optional components such as chemicals used or produced in forming the aldehyde reactant in upstream processes such as dissolved gases, acids, and solvents such as 2,2,4-trimethyl-1,3-pentanediol monoisobutyrate, and dioctyl terephthalate and the like. Preferably, the aldehyde feed stream includes at least 40 mole percent of at least one aldehyde based on the total moles of the aldehyde feed stream.

In an embodiment of the present invention, the method of the present invention further includes the step of feeding a catalyst feed stream that includes a catalyst into the reaction zone and forming a heavy reaction zone effluent that includes an enal and catalyst. In this embodiment, the catalyst is preferably a homogenous catalyst and more preferably an aldol condensation catalyst (such that the enal in the enal-containing reaction mixture is preferably formed via aldol condensation). Suitable homogenous catalysts for use in the method of the present invention include aqueous bases, with aqueous sodium hydroxide being particularly preferred. In an embodiment, the method of the present invention may optionally include combining the catalyst feed stream with the aldehyde feed stream to form a combined feed.

In another embodiment of the present invention, the reaction zone of the feeding step (a) includes a heterogeneous catalyst. Suitable heterogeneous catalysts for the method of the present invention include base functionalized catalysts, with hydrotalcite style catalysts being particularly preferred.

Step (b) of the method of the present invention includes reacting at least one aldehyde reactant in the reaction zone in the presence of a catalyst to form a light reaction zone effluent comprising an enal and unreacted aldehyde reactant. The light reaction zone effluent may also optionally include light feed impurities and water. As noted above, the term "effluent", as used herein, is intended to generally refer to a composition or mixture (i) present in the reaction zone as well as (ii) exiting the reaction zone. It is in this reacting step (b) that the at least one aldehyde reactant is catalytically converted to enal, preferably via aldol condensation. Preferably, the reaction zone in step (b) contains at least one theoretical stage, and more preferably a plurality of theoretical stages. As one skilled in the art will appreciate, a "theoretical stage" refers to a hypothetical zone or stage in which a mixture of two or more phases (e.g. liquid-vapor) approach a thermodynamic equilibrium with each other with the thermodynamic equilibrium based on the overall fugacity of the liquid phase being equal to the overall fugacity of the vapor phase. A theoretical stage is also sometimes referred to in the art as an equilibrium stage, ideal stage, theoretical tray, perfect stage or theoretical plate.

One of ordinary skill will appreciate generally that the products formed by a reaction depend on selection of the reactants and more particularly that the type of enal in the enal-containing reaction mixture formed in reacting step (b) depends on the selection of the at least one aldehyde reactant fed in feeding step (a). For example, when the at least one aldehyde is propionaldehyde, the enal is C6 enal. Similarly, when the at least one aldehyde is a butyraldehyde, the enal is a C8 enal. When the aldehyde feed stream includes two or more aldehyde reactants or a mix of aldehydes, the light reaction zone effluent and the enal-containing reaction mixture includes a corresponding mix of two or more enals. When the aldehyde feed stream includes at least one aldehyde reactant and at least one alcohol, the light reaction zone effluent and the enal-containing reaction mixture includes a mix of acetals.

Step (c) of the method of the present invention includes purifying the enal-containing reaction zone effluent in a first separation zone within the single enclosed unit to form an enal-rich product mixture and a residual unreacted aldehyde mixture. In an embodiment, the purifying step (c) includes subjecting the light reaction zone effluent to staged separation, for example distillation, using at least one theoretical stage, and preferably a plurality of theoretical stages. The precise conditions for approaching thermodynamic equilibrium, as well as the specific number of theoretical stages most useful for practicing the method of the present invention, may vary depending on a number of factors such as, for example, the identity and concentration of the components of the enal-containing reaction zone effluent, the characteristics of those components such as boiling point, the internal flow rates and temperatures of material within the first separation zone and the single enclosed unit, the vapor-liquid contacting hardware and the like. In an embodiment, the method of the present invention further includes feeding the residual unreacted aldehyde mixture to said reaction zone. In an embodiment, the method of the present invention further includes combining the residual unreacted aldehyde mixture with the aldehyde feed stream in feeding step (a).

Step (d) of the method of the present invention includes collecting from the single enclosed unit or vessel at least a portion of said enal-rich product mixture; wherein said collected portion includes at least 60% by weight, more preferably at least 80% by weight, enal based on the total weight of the organic fraction of the enal-rich product mixture. An important and unexpected benefit of the present invention, as demonstrated in the Examples set forth below, is that the method of the present invention surprisingly achieves approximately 20% higher per-pass conversion and about 25% lower energy consumption over the prior art aldehyde-to-enal conversion methods while employing markedly fewer pieces of equipment (which translates to lower capital cost).

In an embodiment where the method of the present invention further includes the step of feeding a catalyst feed stream that includes a catalyst into the reaction zone and forming a heavy reaction zone effluent that includes an enal and catalyst, the method of the present invention preferably further includes the step of purifying said heavy reaction zone effluent in a second separation zone contained within said single enclosed unit to form a heavy byproduct mixture which includes homogenous catalyst and an enal-containing mixture. The step of purifying said heavy reaction zone effluent in a second separation zone contained within said single enclosed unit to form a heavy byproduct mixture and an enal-containing mixture preferably includes subjecting the heavy reaction zone effluent to staged separation, commonly referred to as distillation, using at least one theoretical stage, and preferably a plurality of theoretical stages.

In an embodiment of the method of the present invention, the reaction zone is contained within the enclosed unit or vessel and is distinct from the first separation zone and, in an embodiment, the second separation zone. The phrase "distinct from" is used to connote that, while components may flow between zones, the spatial volume referred to herein as a zone (e.g., the reaction zone) is discrete and separate from the spatial volume of one or more other zones (e.g., the first separation zone and, in an embodiment, the second separation zone). Accordingly, in embodiment, the reacting step (b) is performed within the enclosed unit, in isolation from purifying step (c). Similarly, in an embodiment, the reacting step (b) is performed within the enclosed unit, in isolation from the step of purifying the heavy reaction zone effluent in a second separation zone within said single enclosed unit to form a heavy byproduct mixture that includes homogeneous catalyst and an enal-containing mixture. With regards to the isolation of the reacting step, it will be appreciated by one of ordinary skill in the art that such isolation is achieved at least in part through having the reaction zone distinct from the first separation zone and, in an embodiment, the second separation zone. Further, isolation of the reacting step is facilitated through minimization of aldehyde reactant in the heavy reaction zone effluent. Nonetheless, it will also be appreciated that unintended enal-forming side-reactions may incidentally occur outside the reaction zone, to the extent for example that unreacted aldehyde is present, but that purposeful formation of enal is focused on the reacting step performed in the reaction zone.

In an embodiment, first separation zone may be distinct from second separation zone and, accordingly, purifying step (c) is performed in isolation from the step of the step of purifying the heavy reaction zone effluent to form a heavy byproduct mixture that includes homogeneous catalyst and an enal-containing mixture. In this embodiment, a relevant distinction is that the light reaction zone effluent generally includes an enal and materials with a boiling point lower than the boiling point of the enal while the heavy reaction zone effluent includes an enal and materials with a boiling point higher than that of the enal.

Preferably, the reacting step (b) and purifying step (c) are performed in a single enclosed piece of equipment or enclosed unit or enclosed vessel. Further, the step of purifying the heavy reaction zone effluent in a second separation zone contained within said single enclosed unit to form a heavy byproduct mixture that includes homogeneous catalyst and an enal-containing mixture is performed within the same single enclosed unit or vessel as reacting step (b) and purifying step (c). One of ordinary skill will appreciate that, while at least some of the steps of the method of the present invention has been alphanumerically labeled for the sake of convenience, such labeling does not and is not intended to express directly or through inference that the steps are sequential or, if performed sequentially, that a particular sequence is required. Indeed, a person of ordinary skill will further appreciate that, particularly in a continuous operation of equipment in accordance with the method of the present invention, two or more steps may be performed simultaneously.

FIGS. 2 through 5 generally illustrate suitable single enclosed pieces of equipment or enclosed units or unitary integral units for practicing the method of the present invention. Enclosed unit or enclosed vessel or unitary integral unit 10 includes an outer shell 15 with top end 12, bottom end 13 that is opposite top end 12, interior 14 and dividing wall 20 extending longitudinally within the interior 14 of unit 10. Reaction zone 35 is at least partially defined longitudinally by a dividing wall 20 that extends longitudinally within the enclosed unit 10 and typically horizontally by a volume of contacting or packing material with a top 25 and bottom 30, all of which is contained within enclosed unit 10. In an embodiment, the reaction zone 35 top 25 may be located just above the catalyst feed stream 65 entry point 66 and the bottom 30 may be located just below the aldehyde feed stream 60 entry point 61. Enclosed unit 10 may further include a first separation zone 40 in the interior 14 generally at top end 12 and a second separation zone 50 in the interior 14 generally at bottom end 13. Each of reaction zone 35, first separation zone 40 and second separation zone 50 are contained within enclosed unit 10. Particularly suitable units for the enclosed unit 10 are known in the art as "divided wall" or "dividing wall" reactive distillation columns. Such devices are described for example in U.S. Pat. Nos. 8,952, 189; 6,930,206 and 8,764,946, the contents and description of which are hereby incorporated herein by reference.

Figure 2:
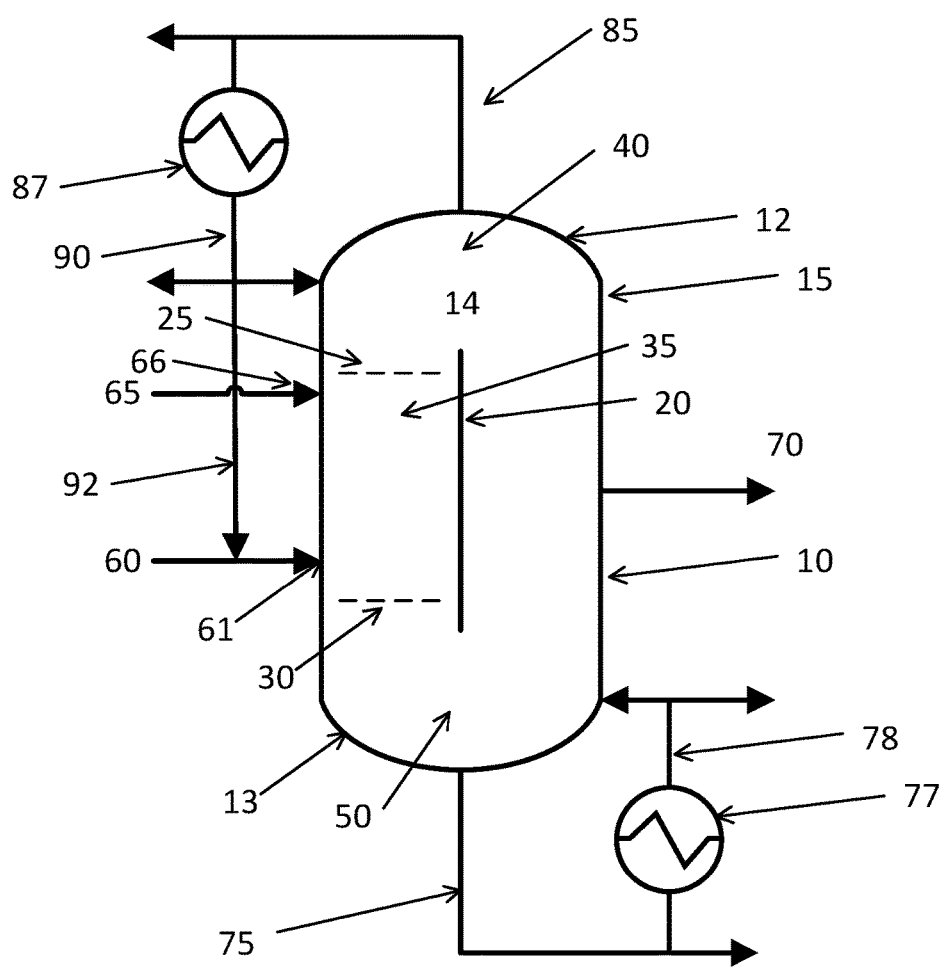
FIG. 2 is a schematic representation of an embodiment of an enclosed single unit useful for performing the method of present invention depicted with optional streams.

In the embodiment shown in FIG. 2, dividing wall 20 extends longitudinally in interior 14 of unit 10. It will be appreciated that the specific details of the dividing wall 20, such as for example precise location and length, will depend on a number of factors, including for example feed composition and component concentration, operating temperatures and pressures and other variables. In one embodiment, depicted in FIG. 3, dividing wall 20 extends to the top end 12 of unit 10 and connects to the outer enclosure 15 of unit 10. In the embodiments shown in FIGS. 4 and 5, dividing wall 20 extends to the bottom end 13 of unit 10 and connects to its outer enclosure 15.

In operation of an embodiment, aldehyde feed stream 60 that includes at least one aldehyde reactant and catalyst feed stream 65 that includes a catalyst are fed into reaction zone 35 in which reacting step (a) occurs to form a light reaction zone effluent that includes an enal and unreacted aldehyde reactant and a heavy reaction zone effluent that includes an enal and catalyst. In an embodiment, the reaction zone 35 will extend from just above the catalyst feed stream 65 entry point 66 to just below the aldehyde feed stream 60 entry point 61. A light reaction zone effluent that includes enal and unreacted aldehyde reactant exits the reaction zone and is purified in first separation zone 40 to form an enal-rich product mixture and a residual unreacted aldehyde mixture. At least a portion of the enal-rich product mixture is collected from the enclosed unit as shown generally at 70, with the collected portion including at least 60% by weight enal, preferably at least 80% by weight enal, based on the total weight of the organic fraction of the enal-rich product mixture. A heavy reaction zone effluent that includes an enal and catalyst exits the reaction zone and is purified in second separation zone 50 to form a catalyst byproduct mixture and an enal-containing mixture.

One will appreciate that, in addition to the enal-rich product mixture, a number of side-streams may optionally be collected from operation of the method of the present invention. Further, some of these collected side-streams may be recycled to the enclosed unit 10 for further processing within the scope of the present invention. Non-limiting examples are depicted in FIGS. 2 through 5. As shown in the embodiment that depicted in FIG. 2, a heavies effluent 75 which includes primarily catalyst, enals, and water is removed from second separation zone 50 and then collected with a portion optionally passed through a boiler 77 with a resulting separated heavies stream 78 collected, returned to second separation zone 50 or a combination thereof. In this embodiment, the method of the present invention may include removing a heavies effluent which includes primarily catalyst, enals, and water from second separation zone; optionally separating the heavies effluent into separated heavies streams; and one or more of collecting and returning to the second separation zone at least one separated heavies stream. Similarly, a lights effluent 85 is at least partially condensed internally or removed from first separation zone 40 with a portion optionally passed through a condenser 87 with a resulting separated lights stream 90 collected, returned to the first separation zone, the reaction zone or a combination thereof. In this arrangement, separated lights stream 90 may be a residual unreacted aldehyde mixture and the method of the present invention may include feeding the residual unreacted aldehyde mixture to the reaction zone or combining the residual unreacted aldehyde mixture with the aldehyde feed stream as shown at 92. A separated lights stream may also be a second or alternate enal-rich product mixture that preferably includes at least 60% by weight, more preferably at least 80% by weight, enal based on the total weight of organic fraction of the enal-rich product mixture.

Figure 3:
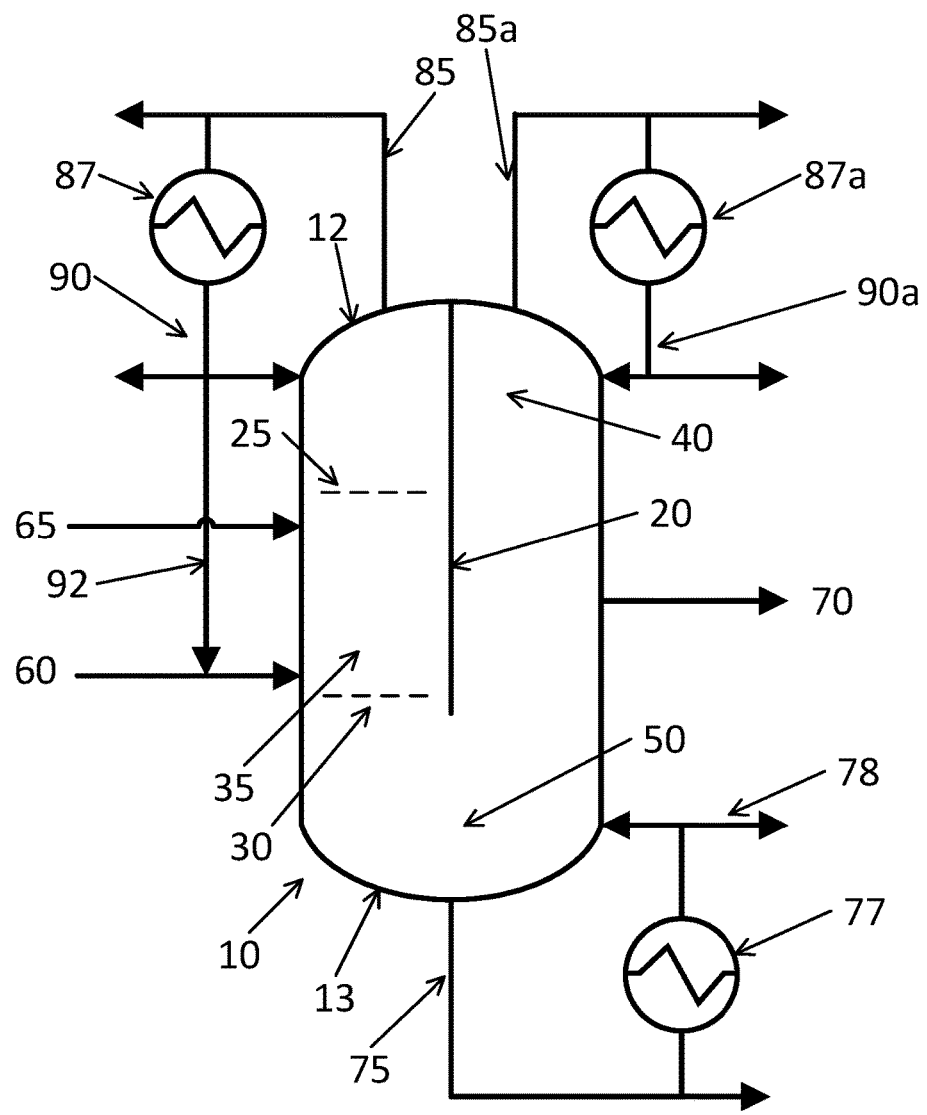
FIG. 3 is a schematic representation of another embodiment of an enclosed single unit useful for performing the method of present invention depicted with optional streams.
Figure 4:
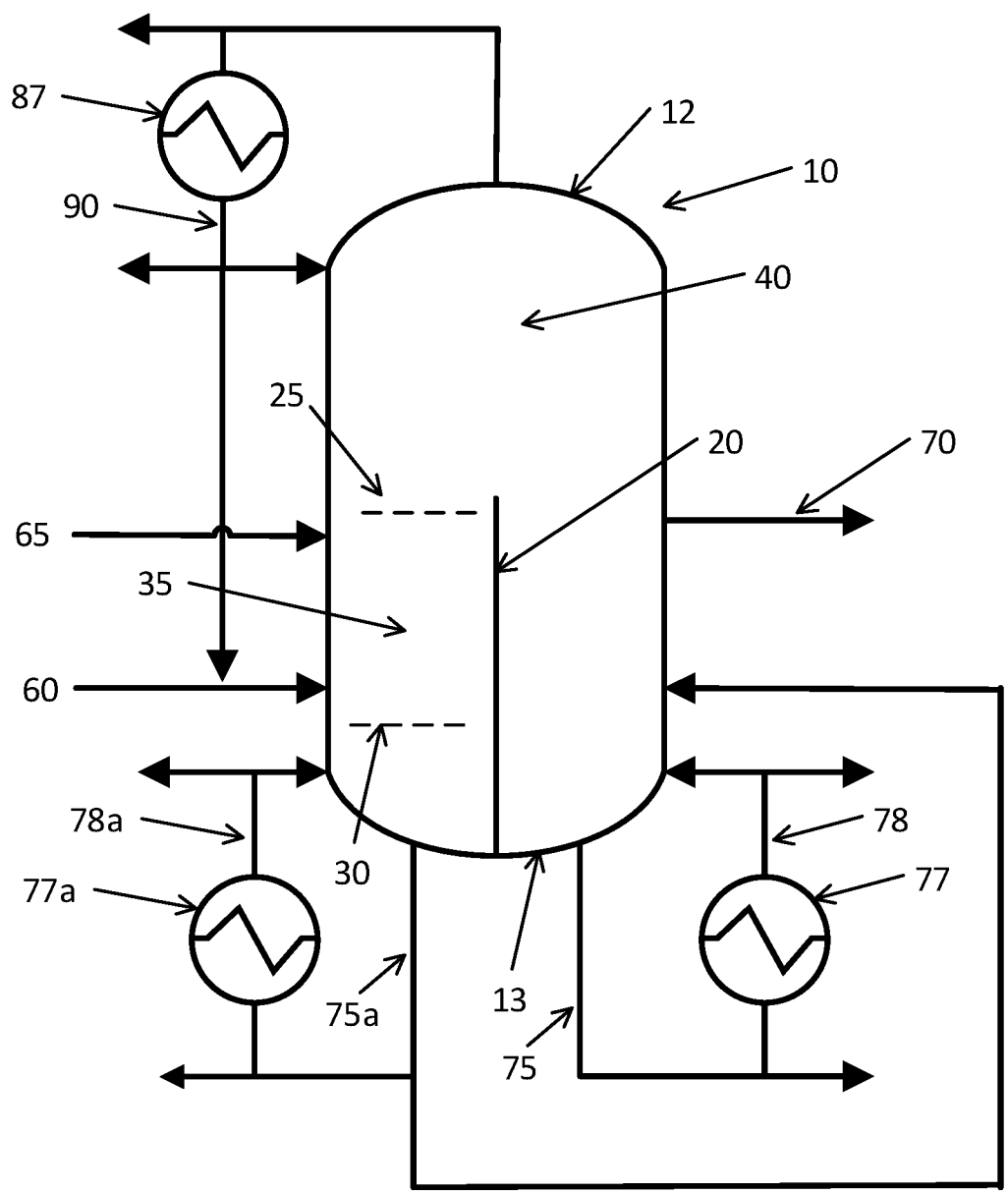
FIG. 4 is a schematic representation of yet another embodiment of an enclosed single unit useful for performing the method of present invention depicted with optional streams.
Figure 5:
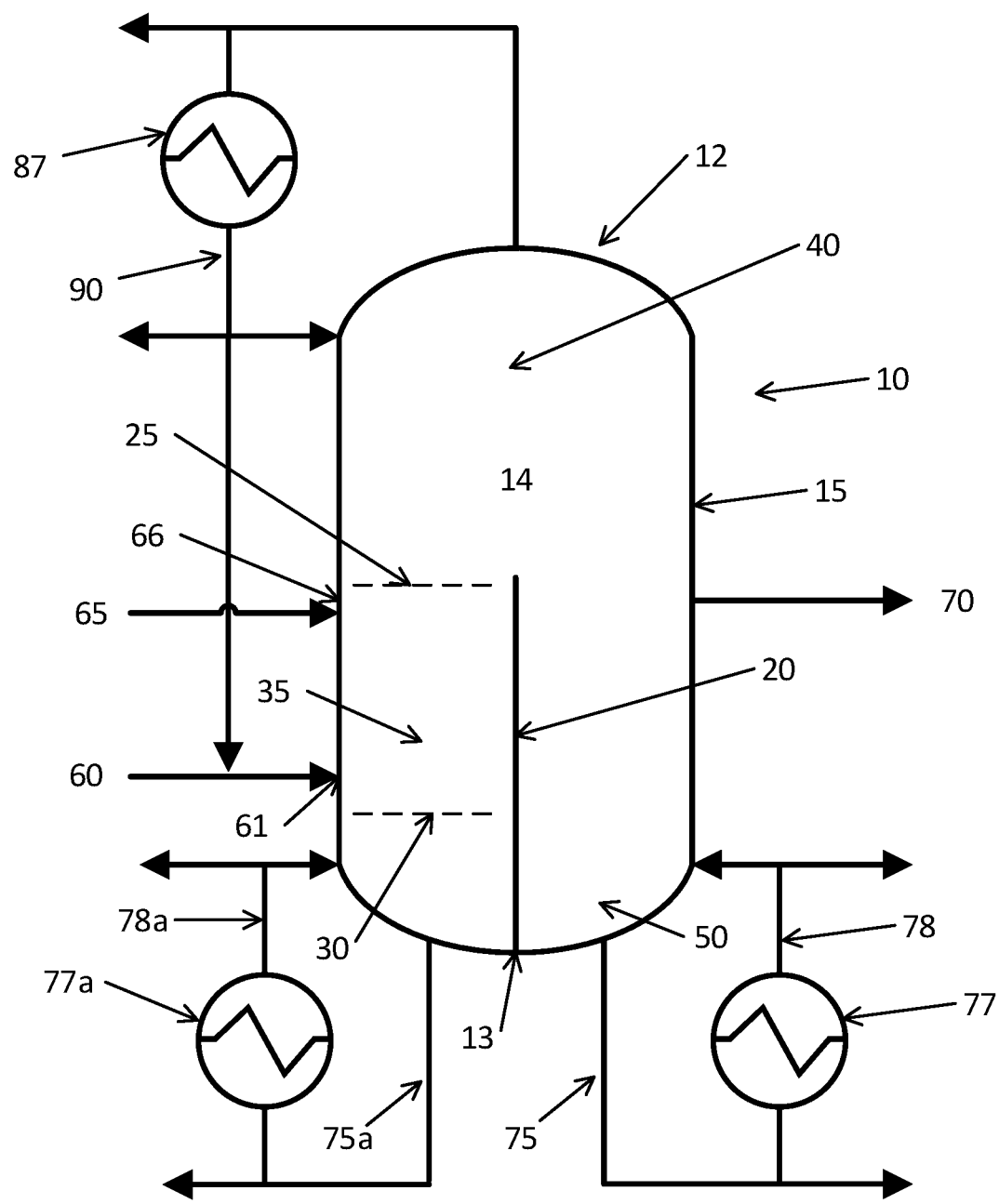
FIG. 5 is a schematic representation of the embodiment of an enclosed single unit useful for performing the method of present invention depicted in FIG. 4 but with a different optional streams configuration

As shown in the embodiment that is depicted in FIG. 3, multiple optional lights effluents 85 and 85*a* may be collected from first separation zone 40, with a portion passed through condensers 87 and 87*a* with separated lights streams 90 and 90*a* collected, returned to the first separation zone, the reaction zone or a combination thereof. As shown in the embodiments that are depicted in FIGS. 4 and 5, multiple optional heavies effluents 75 and 75*a* may be collected from second separation 50, with a portion passed through boilers 77 and 77*a* with separated heavies streams 78 and 78*a*, collected, returned to second separation zone 50 or a combination thereof.

The following examples set forth suitable and/or preferred methods and results in accordance with the invention. It is to be understood, however, that these examples are provided by way of illustration and nothing therein should be taken as a limitation upon the overall scope of the invention. All percentages are by weight unless otherwise specified.

BACKGROUND INFORMATION REGARDING EXAMPLES

Though detailed mathematical analysis may be performed manually to model chemical processes, the use of modern process simulation software is well understood and pervasive throughout the chemical processing industry. Application of process simulation software is especially useful for the modeling of multicomponent distillation processes. The computational approach to simulating the outcome of a given distillation column or process has been well known and thoroughly documented in the literature. An extension to divided wall column distillation is exemplified in the article "Separation of a Mixture by Divided Wall Column Using ASPEN PLUS" by Khushalani, Maheshwari, and Jain in International Journal of Emerging Technology and Advanced Engineering; Volume 4, Issue 8, August 2014. In order to apply the method of Khushalani et. al to simulate the present invention, one of ordinary skill will appreciate that the user must enable reactions in the reactive sections, as exemplified in the article entitled Simulate a Reactive Distillation Column with Aspen Plus® V8.0, and input kinetics of the reaction. The examples herein make use of ASPEN Plus® computer simulations to demonstrate the surprising and unexpected benefits of the present invention. The input for and outputs of the simulations are provided in tables below. The tables below track those species which are of particular commercial interest in the given examples.

Example 1

The software described above was utilized to perform a computer model simulation of the present invention. In the simulation of Example 1, an exemplary feed of 1000 kg/hr. of substantially pure n-butyraldehyde and at 30 degrees Celsius was employed. This feed and a catalyst stream of aqueous caustic solution (sodium hydroxide in water) were introduced into an ASPEN Radfrac™ unit operation block which simulates a distillation process with reaction. This simulation construct is intended to mimic a reaction zone 35 as described herein and shown in FIG. 2. The reaction zone included ten (10) theoretical stages operating at an approximate average pressure of 0.77 bar gauge. The remainder of the simulation included non-reactive ASPEN Radfrac unit operation blocks along with other conventional unit operation blocks such as flow splitter, heaters, etc.

Example 1 results for species of commercial relevance for the present invention are shown in Table 1 below with details and identifications for the various streams for Table 2 set forth in accompanying FIG. 2:

TABLE 1

| | Streams (kg/hr) | | | |
| --- | --- | --- | --- | --- |
| Components | Feeds (60 and 65) | Product (70) | Separated and Collected Heavies | Separated and Collected Lights |
| Water | 4032 | 1992 | 2167 | 17 |
| Sodium Hydroxide | 8 | 0 | 8 | 0 |
| Normal Butyraldehyde | 1000 | 0 | 0 | 3 |
| 2-Ethylhex-2-enal | 0 | 846 | 43 | 10 |

The rate of heat input for the simulation of Example 1 was 10,117 kW.

Example 2

The software described in Example 1 above was utilized to perform a computer model simulation of the present invention using the same input data and conditions as in Example 1 except that the dividing wall extends to the bottom end of unit and connects to its outer enclosure. Results for the simulation are detailed in Table 2 below with details and identifications for the various streams for Table 2 set forth in accompanying FIG. 4.

TABLE 2

| | Streams (kg/hr) | | | |
|---|---|---|---|---|
| Components | Feeds (60 and 65) | Product (70) | Separated and Collected Heavies | Separated and Collected Lights |
| Water | 4032 | 1977 | 2160 | 18 |
| Sodium Hydroxide | 8 | 0 | 8 | 0 |
| Normal Butyraldehyde | 1000 | 0 | 0 | 2 |
| 2-Ethylhex-2-enal | 0 | 850 | 0 | 10 |

The rate of heat input for the simulation of Example 2 was 10,178 kW.

Example 3

As a control, the software described in Example 1 above was utilized to perform a computer model simulation of a typical prior art aldol condensation process employing separate reactor and distillation units as shown in FIG. 1. The same feed composition as in Example 1 was used; however, for this control example, a reactor (ASPEN Plus CSTR unit operation block) was used simulate the reaction separate from the ASPEN Radfrac unit operation blocks which simulate the non-reactive distillation process. In this instance, two separate distillation columns operated in series were configured to parallel the separation of aqueous catalyst solution from the enal product as shown in FIG. 1. Results for the simulation are detailed in Table 3 below with details and identifications for the various streams for Table 3 set forth in accompanying FIG. 5.

TABLE 3

| | Streams (kg/hr) | | | |
|---|---|---|---|---|
| Components | Feeds (60 and 65) | Product (70) | Separated and Collected Heavies | Separated and Collected Lights |
| Water | 4032 | 1523 | 2562 | 45 |
| Sodium Hydroxide | 8 | 0 | 8 | 0 |
| Normal Butyraldehyde | 1000 | 1 | 0 | 215 |
| 2-Ethylhex-2-enal | 0 | 679 | 0 | 8 |

The rate of heat input for the simulation of Example 3 was 10,327 kW.

As evidenced by the data provided in the above Tables, the method of the present invention surprising achieves approximately 20% higher yield and 25% lower energy consumption over the prior art aldol condensation methods while employing markedly fewer pieces of equipment.

The foregoing description of various embodiments of the invention has been presented for purposes of illustration and description. It is not intended to be exhaustive or to limit the invention to the precise embodiments disclosed. Numerous modifications or variations are possible in light of the above teachings. The embodiments discussed were chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

That which is claimed is:

1. A method for producing an enal-rich product mixture from an aldehyde feed stream in a single enclosed unit, said method comprising
   (a) feeding an aldehyde feed stream comprising at least one aldehyde reactant into a reaction zone contained within said single enclosed unit;
   (b) reacting said at least one aldehyde reactant in said reaction zone in the presence of a catalyst to form a light reaction zone effluent comprising an enal and unreacted aldehyde reactant;
   (c) purifying said light reaction zone effluent in a first separation zone within said single enclosed unit to form an enal-rich product mixture and a residual unreacted aldehyde mixture; and
   (d) collecting from said single enclosed unit at least a portion of said enal-rich product mixture; wherein said collected portion includes at least 60% by weight enal based on the total weight of the organic fraction of said enal-rich product mixture.

2. The method of claim 1 further comprising the step of feeding a catalyst feed stream comprising a homogeneous catalyst into said reaction zone and forming a heavy reaction zone effluent comprising enal and said homogeneous catalyst.

3. The method of claim 1 wherein said reaction zone comprises a heterogeneous catalyst.

4. The method of claim 1 wherein said aldehyde feed stream comprises includes two or more aldehydes.

5. The method of claim 1 wherein said aldehyde feed stream further comprises at least one alcohol.

6. The method of claim 1 wherein said aldehyde is selected from the group consisting of acetaldehyde, propionaldehyde, butyraldehyde, valeraldehyde, capronaldehyde and mixtures thereof.

7. The method of claim 6 wherein said aldehyde is propionaldehyde or butyraldehyde.

8. The method of claim 7 wherein said aldehyde is propionaldehyde and said enal is C6 enal.

9. The method of claim 7 wherein said aldehyde is butyraldehyde and said enal is C8 enal.

10. The method of claim 2 further comprising purifying said heavy reaction zone effluent in a second separation zone contained within said single enclosed unit to form a catalyst byproduct mixture and an enal-containing mixture.

11. The method of claim 1 further comprising feeding said residual unreacted aldehyde mixture to said reaction zone.

12. The method of claim 1 further comprising combining said residual unreacted aldehyde mixture with said aldehyde feed stream.

13. The method of claim 1 wherein said reaction zone is distinct from said first separation zone.

14. The method of claim 10 wherein said reaction zone is distinct from said first separation zone and said second separation zone.

15. The method of claim 1 wherein said purifying step (c) comprises subjecting said light reaction zone effluent to staged separation using at least one theoretical stage.

16. The method of claim 15 wherein said purifying step (c) comprises subjecting said light reaction zone effluent to staged separation using a plurality of theoretical stages.

17. The method of claim 1 wherein said reaction zone is at least partially defined longitudinally by a dividing wall that extends longitudinally within said enclosed unit.

18. The method of claim 2 wherein said homogeneous catalyst is an aqueous base.

19. The method of claim 18 wherein said aqueous base is aqueous sodium hydroxide.

\* \* \* \* \*